United States Patent [19]

Hara

[11] Patent Number: 5,206,893
[45] Date of Patent: Apr. 27, 1993

[54] RADIOTHERAPEUTIC APPARATUS HAVING THREE DIMENSIONAL LIGHT MARKS

[75] Inventor: Yukihiro Hara, Tokyo, Japan

[73] Assignee: Yokogawa Medical Systems, Limited, Tokyo, Japan

[21] Appl. No.: 778,212

[22] PCT Filed: Jun. 29, 1990

[86] PCT No.: PCT/JP90/00856
§ 371 Date: Dec. 9, 1991
§ 102(e) Date: Dec. 9, 1991

[87] PCT Pub. No.: WO91/00057
PCT Pub. Date: Jan. 10, 1991

[30] Foreign Application Priority Data

Jun. 30, 1989 [JP] Japan .................................. 1-170746

[51] Int. Cl.⁵ .............................................. A61N 5/10
[52] U.S. Cl. .......................................... 378/65; 378/68; 378/151; 378/164; 378/206
[58] Field of Search .................. 378/65, 62, 68, 205, 378/206, 4, 21, 901, 147, 162, 150, 163, 151, 164

[56] References Cited

U.S. PATENT DOCUMENTS

| | | | |
|---|---|---|---|
| 3,991,310 | 11/1976 | Morrison | 378/65 |
| 4,256,966 | 3/1981 | Heinz | 378/65 |
| 4,558,458 | 12/1985 | Katsumata et al. | 378/206 |
| 4,835,688 | 5/1989 | Kimura | 378/901 |
| 4,882,741 | 11/1989 | Brown | 378/206 |
| 5,031,203 | 7/1991 | Trecha | 378/205 |
| 5,039,867 | 8/1991 | Nishihara et al. | 378/65 |
| 5,090,401 | 2/1992 | Schwieker | 378/205 |

FOREIGN PATENT DOCUMENTS

| | | |
|---|---|---|
| 137615 | 9/1988 | Japan . |
| 1-65046 | 4/1989 | Japan . |
| 1-151467 | 6/1989 | Japan . |
| 177738 | 11/1989 | Japan . |

Primary Examiner—David P. Porta
Assistant Examiner—Kim-Kwok Chu
Attorney, Agent, or Firm—Moonray Kojima

[57] ABSTRACT

An object of the present invention is to realize a radiotherapeutic system whereby the process from the stage of making a diagnosis of a body to be examined for obtaining information of position, size, shape etc. of the diseased part and making up a therapeutic plan of such items as the area to be irradiated by a radiation to the stage of positioning of the area to be irradiated on the body being examined and applying the radiation to the body can be reasonably executed with little trouble.

The present invention is characterized by that tomograms are taken by means of an X-ray CT, three-dimensional coordinates of the center position of the region of interest to which the radiotherapy is to be applied and a perspective image of the region of interest similar to the perspective image obtained by means of an X-ray simulator are obtained by calculation performed by a calculating device with image data of tomograms, the reference positions for application of the therapy are marked on the body being examined according to indications given by a positioning device on the basis of the three-dimensional coordinates of the center position of the region of interest, and the radiation collimator of the therapeutic apparatus is controlled by a therapeutic apparatus controller on the basis of the calculated perspective image of the region of interest.

2 Claims, 4 Drawing Sheets

FIG.4
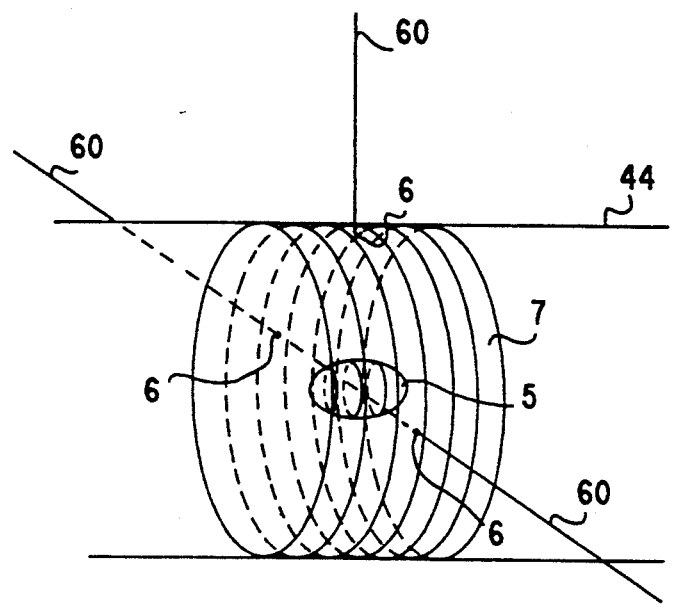
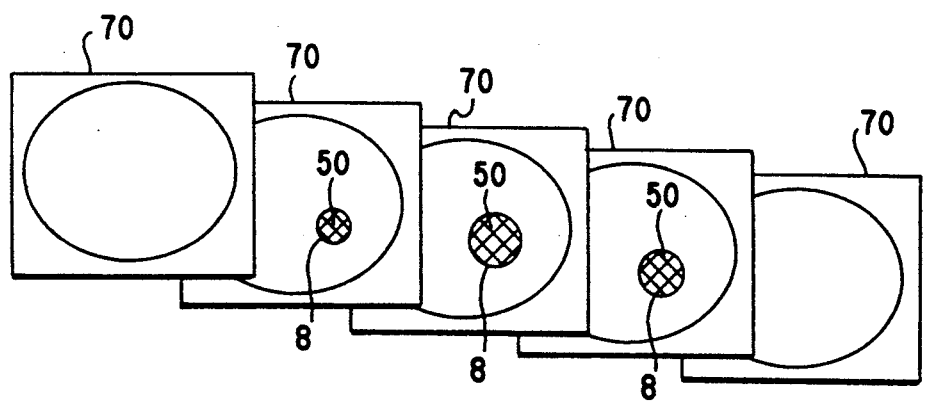
FIG.5

RADIOTHERAPEUTIC APPARATUS HAVING THREE DIMENSIONAL LIGHT MARKS

TECHNICAL FIELD

The present invention relates to a radiotherapeutic system constituted of a radiotherapeutic apparatus and a therapeutic planning apparatus in combination.

BACKGROUND ART

In the latter half of 1960's, a linear accelerator (hereinafter referred to as "linac") appeared as means for treating cancer. Because of its simple acceleration principle and enhanced reliability on its microwave source, it gained a high evaluation as practical radiotherapeutic apparatus and rapidly came into use. Then, with the development of various high-energy radiotherapies, great importance has come to be placed on highly accurate therapeutic planning. The overall process of a radiotherapy includes the following stages. The first is the stage of diagnosis, that is, to correctly detect position, size, shape, etc. of the diseased part by utilizing, for example, X-ray CT images. The second is the stage of making up a therapeutic plan, that is, to decide the kind of curing radiation, the dose, the direction of irradiation, the area to be irradiated, etc., on the basis of various data obtained at the time of diagnosis. The third is the stage of execution of the medical treatment, that is, to position the area of irradiation on the body of a person being examined, confirm it, and apply the radiation thereto. The fourth is the stage of management, that is, collation, recording, retention, etc. of data obtained in the stages of diagnosis, planning, and execution of medical treatment.

In order to define the area of irradiation for radiotherapy, tomographic images obtained by an X-ray CT etc. and a perspective image obtained by an X-ray simulator have so far been utilized. The interior of the body being examined can be shown with high contrast and resolution in the tomographic image by means of the X-ray CT, the diseased part (region of interest) can be specified in the tomographic image relatively easily. In the perspective image by means of the X-ray simulator, the visual point for perspective viewing is set in concurrence with the center of radiation of the curing radiation. Therefore, the region of interest in the perspective image can be easily brought into concurrence with the relative part on the surface of the body being examined. At the time of execution of the radiotherapy, the body being examined is moved onto the table of the therapeutic apparatus, the perspective image obtained by means of the X-ray simulator on a film is projected with light on the surface of the body being examined, the region of diseased part to be treated is drawn on the body being examined by tracing the projected image with a felt-tip pen or the like, and then the collimator aperture at the radiation emitting window is adjusted to the region of the diseased part drawn on the body being examined, and thereafter, the radiation from the radiation source is applied to the body being examined.

Since, as described above, tomograms are taken with an X-ray CT, the body being examined is then moved into an X-ray simulator to have a photograph of perspective image taken, the body being examined is then moved onto the table of a therapeutic apparatus to have the perspective image in a film projected on the surface of the body being examined so that the region of diseased part to be treated is marked with a felt-tip pen by tracing the projected image, that is, various operations are performed by the use of separate apparatuses, much labor and time have so far been taken. Further, many operations, such as the setting of the film of the perspective image on the therapeutic apparatus and the setting of the collimator of the therapeutic apparatus, have relied on manual work of the operator. Therefor, much time and labor have been required for such operations and this has been the cause of personal mistakes.

DISCLOSURE OF THE INVENTION

An object of the present invention is to realize a radiotherapeutic system whereby the process from the stage of making a diagnosis of a body to be examined for obtaining information of position, size, shape etc. of the diseased part and making up a therapeutic plan of such items as the area to be irradiated by a radiation to the stage of positioning of the area to be irradiated on the body being examined and applying the radiation to the body can be reasonably executed with little trouble.

The present invention is characterized by that tomograms are taken by means of an X-ray CT, three-dimensional coordinates of the center position of the region of interest to which the radiotherapy is to be applied and a perspective image of the region of interest similar to the perspective image obtained by means of an X-ray simulator are obtained by calculation performed by a calculating device with image data of tomograms, the reference positions for application of the therapy are marked on the body being examined according to indications given by a positioning device on the basis of the three-dimensional coordinates of the center position of the region of interest, and the radiation collimator of the therapeutic apparatus is controlled by a therapeutic apparatus controller on the basis of the calculated perspective image of the region of interest.

BRIEF DESCRIPTION OF THE DRAWINGS

FIG. 4 to FIG. 6 are explanatory diagrams of a method for obtaining a calculated perspective image.

BEST MODE FOR CARRYING OUT THE INVENTION

Figure 1:
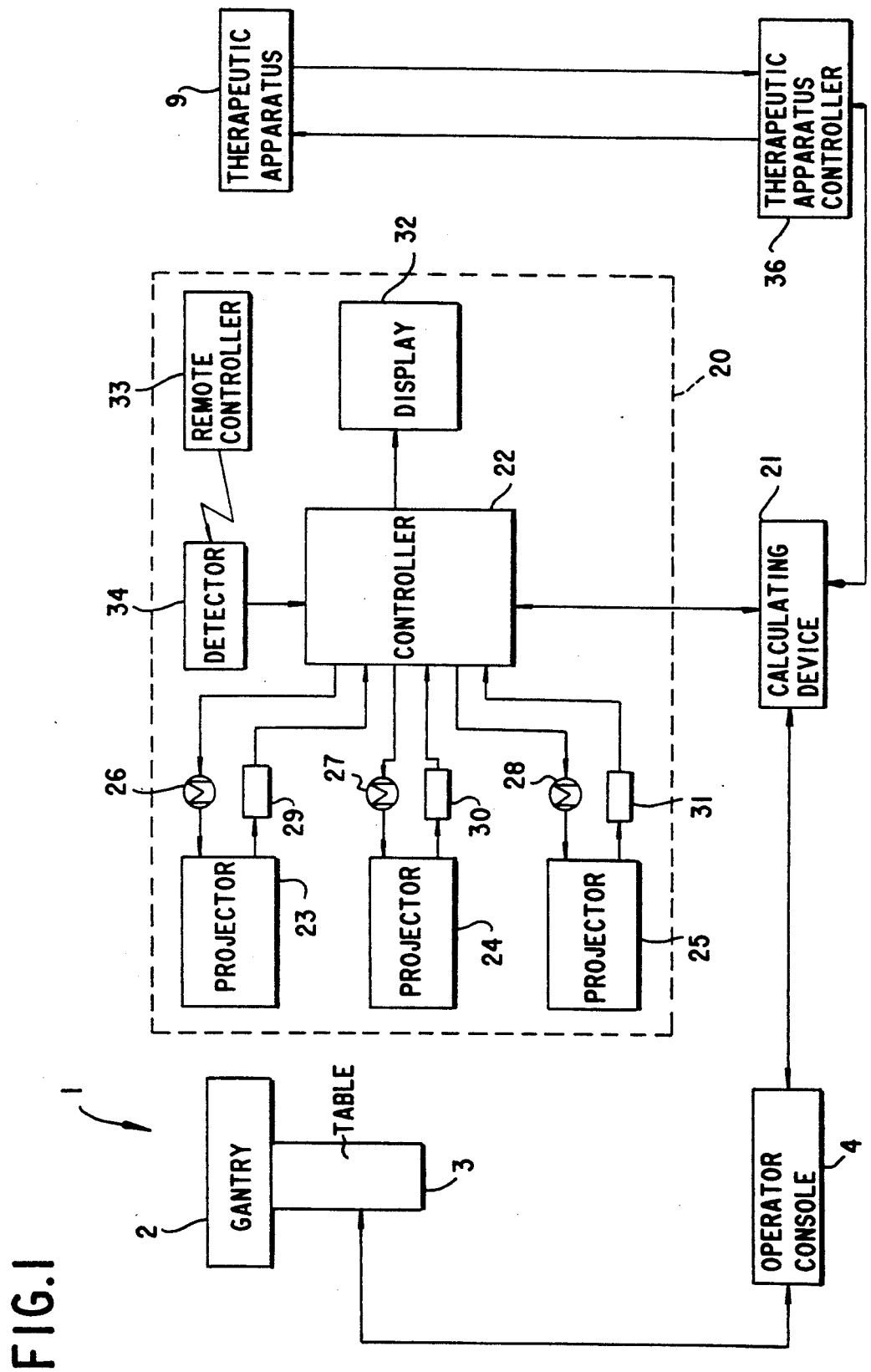
FIG. 1 is a block diagram showing the structure of an embodiment of the present invention.
Figure 2:
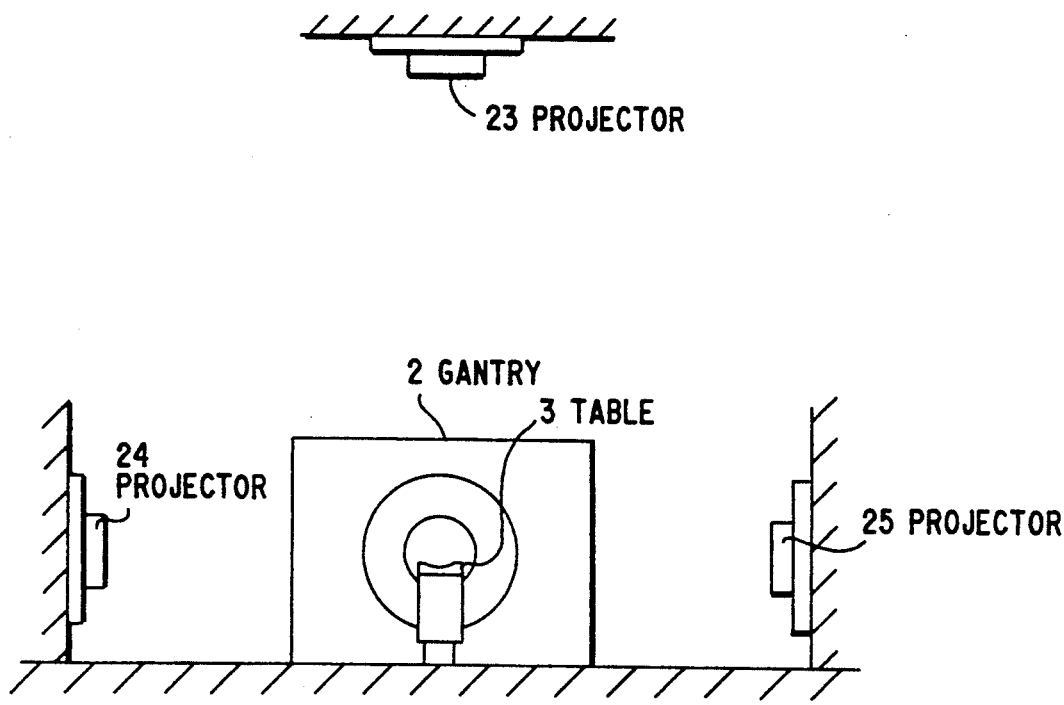
FIG. 2 is a diagram showing an arrangement of projectors in a positioning apparatus.

FIG. 1 is a block diagram showing the configuration of an embodiment of the present invention. Referring to FIG. 1, reference numeral 1 denotes an X-ray CT which is formed of a gantry 2, a table 3, and an operator console 4. Reference numeral 9 denotes a therapeutic apparatus, for which a linac is supposed to be used in the present example. Reference numeral 20 denotes a positioning device and 21 denotes a calculating device. The calculating device 21 receives tomographic image data of the body being examined obtained by the X-ray CT and the region-of-interest data specified by the diagnostician from the operator console 4 and obtains by calculation with these data three-dimensional coordinates of the center position of the region of interest and the perspective image of the region of interest. Reference numeral 22 denotes a controller included in the positioning device 20 for controlling positions of projectors 23, 24, and 25 in accordance with the coordinate data of the center of the region of interest supplied from the calculating device 21. The controller 22 moves the projectors 23, 24, and 25 through motors 26, 27, and 28, respectively. FIG. 2 shows relative arrangement between the projectors 23, 24, and 25 and the X-ray CT 1. The projector 23 is installed on the ceiling of the CT chamber and projects a cross mark on the body being examined on the table 3 from above, and it is arranged to be movable leftward and rightward in the drawing and positioned according to the y-coordinate data of the three-dimensional coordinate data. The projector 24 is installed on the left-hand wall of the CT chamber and the projector 25 is installed on the right-hand wall of the CT chamber and project cross marks on the left side and the right side of the body being examined, respectively, and they are arranged to be movable up and down in the drawing and positioned according to the z-coordinate data of the three-dimensional coordinate data. Reference numerals 29, 30, and 31 denote position sensors for detecting positions of the projectors 23, 24, and 25, respectively, and feeding back the detected data to the controller 22. Reference numeral 32 denotes a display for displaying positions of the projectors 23, 24, and 25. Reference numeral 33 denotes a remote controller for externally inputting various conditions to the controller 22. Command signals from the remote controller are adapted to be input to the controller 22 in the form of infrared radiation or the like through a detector 34.

Figure 3:
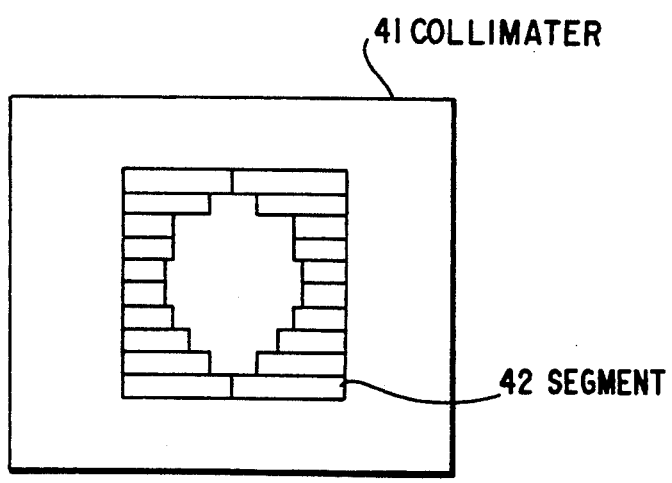
FIG. 3 is a diagram of a radiation collimator of a therapeutic apparatus.

Reference numeral 36 denotes a therapeutic apparatus controller for controlling the aperture of the collimator at the radiation emitting window of the therapeutic apparatus 9 on the basis of a calculated perspective image of the region of interest received from the calculating device 21. An example of the collimator 41 is shown in FIG. 3. The collimator 41 is formed of lead and its several movable segments 42 of lead are adapted to form a variable aperture. By the control of the aperture of the collimator executed by the therapeutic apparatus controller 36, the area of irradiation can be made not only into a simple square form but also into a complex form corresponding to the form of the region of interest. In the therapeutic apparatus controller 36, there is provided a CRT (not shown), on which the three-dimensional coordinates of the center position of the region of interest and the perspective image calculated by the calculating device 21 are adapted to be displayed. The therapeutic apparatus controller 36 is supplied with a perspective image (linacgraphy) of the body being examined taken by the therapeutic apparatus 9 under the same conditions as the treating conditions and this image is also adapted to be displayed on the CRT. Thus, by comparing the calculated perspective image and the linacgraphy with one superposed on the other, it can be checked whether the positioning with respect to the body being examined is in accordance with the therapeutic plan, and it can also be checked, after the treatment has been finished, whether or not the treatment has been carried out in accordance with the therapeutic plan.

Figure 6:
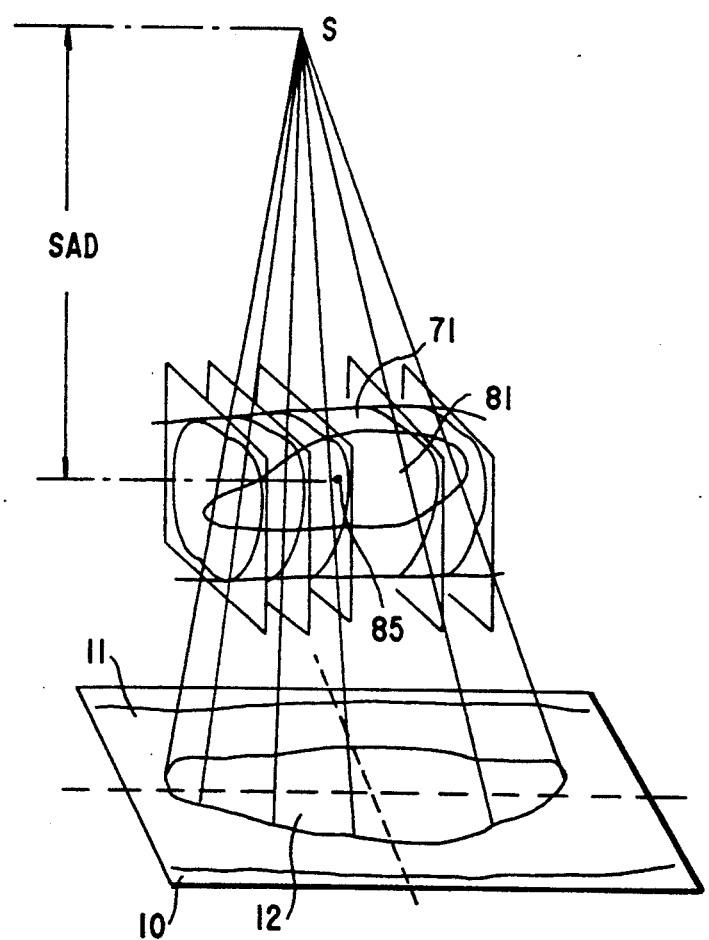

The calculating device 21 obtains the three-dimensional coordinates of the center position of the region of interest from the image data of the X-ray CT 1 according to the following method. FIG. 4 to FIG. 6 are explanatory diagrams of the calculating method. Referring to FIG. 4, reference numeral 44 denotes a body being examined and 5 denotes the pathologic part therein. Reference numeral 7 denotes the position of each of the multislices by the X-ray CT 1. In FIG. 5, reference numerals 70 denote a plurality of tomographic images by the X-ray CT 1, 50 denotes the image of the pathologic part in each tomographic image, and 8 denotes the region of interest established in the tomographic image 70 by the diagnostician. The calculating device 21 obtains the three-dimensional image data for the body being examined as indicated by 71 in FIG. 6 by interpolating a plurality of tomographic images 70 and also obtains the three-dimensional image data 81 of the region of interest by interpolating a plurality of images of the region of interest 8 and further obtains the center position 85 of the three-dimensional region of interest. The above described positions of the projectors 23, 24, and 25 are adjusted according to the three-dimensional coordinates of the center position and three marks 6 are projected on the surface of the body being examined by three rays of light 60 as shown in FIG. 4. The calculating device 21 further sets up an imaginary center position of projection S at a finite distance SAD (Source Axis Distance) from the center 85 of the region of interest and sets up an imaginary plane of projection 10 perpendicular to the straight line connecting the center position of projection S and the center 85 of the region of interest. The center position of projection S is set up so as to have the same geographic relation to the center 85 of the region of interest as that of the radiation source of the radiotherapeutic apparatus 9. Based on such setting, the calculating device 21 obtains a projected image 11 of the body being examined by projecting the three-dimensional data of the body from the imaginary center position of projection S onto the plane of projection 10 and also obtains a projected image 12 of the region of interest by equally projecting the three-dimensional data of the same. This projected image 12, in fact, is the calculated perspective image. This calculated perspective image corresponds to the perspective image which has conventionally been obtained by means of an X-ray simulator. The calculated perspective image is obtained for each of irradiation directions of the therapeutic radiation.

With the described arrangement, the embodiment operates in the following manner. The body being examined is placed on the table 3 of the X-ray CT 1 and a multislice scan is performed. The collected X-ray radiographic data are sent from the gantry 2 to the operator console 4 and image reconstruction is performed by a processor within the operator console 4. The thus reconstructed multiple images are displayed on the display of the operator console and the region of interest is set up in these images by the diagnostician. The plural image data with the region of interest set up therein are transferred to the calculating device 21. The calculating device 21 obtains the three-dimensional coordinates of the center position of the region of interest and sends the y-coordinate and z-coordinate out of them to the controller 22 of the positioning device 20. The controller 22, based on the coordinate data from the calculating device 21, shifts the projector 23 so that the position of the cross mark projected on the body being examined by the projector 23 concurs with the y-coordinate of the center position of the region of interest and also shifts the projectors 24 and 25 so that the positions of the cross marks projected on the body being examined by the projectors 24 and 25 concur with the z-coordinate of the center position of the region of interest. The x-coordinate of the center position of the region of interest is sent from the calculating device 21 to the operator console 4 of the X-ray CT 1. The operator console 4, based on the x-coordinate, shifts the table 3 so that the projected positions of the cross marks projected on the body being examined by the projectors 23, 24, and 25 concur with the x-coordinate. Thus, the positions of the cross marks projected on the body being examined by the three projectors are brought into alignment with the center position of the region of interest. Thereafter, marks are drawn with a felt-tip pen or the like on the surface of the body at three positions where the cross marks are being projected. Sometimes, there occur cases where it is difficult to draw the mark at the right position to be marked on account of the condition of the surface of the body there. In such case, the mark may be drawn at a position a predetermined known distance shifted from the right position.

Then, the body being examined is shifted onto the table of the therapeutic apparatus 9 and the position of the table is adjusted so that the center position of the region of interest determined by the above described three marks on the body being examined is aligned with the center of rotation of the therapeutic gantry. When a mark was drawn a predetermined known distance shifted from the center position of the region of interest, compensation is made for the shifted distance to achieve the alignment. The calculating device 21 transfers the calculated perspective image data of the region of interest to the therapeutic apparatus controller 36. The calculated perspective image is reduced by the scale corresponding to the distance between the radiation source and the collimator. The therapeutic apparatus controller 36, based on the calculated perspective image data supplied from the calculating device 21, moves the segments 42 of the collimator 41 so that the shape of its aperture is adjusted to the shape of the region of interest. Then, the therapeutic apparatus 9 emits the radiation for a short period of time and takes the linacgraphy determined by the shape of the collimator and transfer the video signal for that image to the therapeutic apparatus controller 36. The therapeutic apparatus controller 36 displays the linacgraphy superposed on the calculated perspective image supplied from the calculating device 21 on the CRT. The diagnostician confirms that the body being examined is placed in the right position according to the condition of registration of the two images on the CRT and, thereafter, the radiation is emitted from the therapeutic apparatus 9 for giving treatment.

According to the present invention as described in the foregoing, the process from the stage of taking of tomographic images of a body being examined by means of the X-ray CT and the making up of a therapeutic plan on the basis of the results of the diagnosis to the stage of the treatment of a disease by the therapeutic apparatus can be performed on an on-line basis. Therefore, the work of the operator can be rationalized and mistakes by manual work can be decreased. Further, since the comparison between the linacgraphy and the calculated perspective image can be made easily, the reliability on the making up of the therapeutic plan and execution of the therapy can be enhanced.

Although only the aperture of the collimator of the therapeutic apparatus has been described to be controlled by the therapeutic apparatus controller in the above embodiment, angle, position, etc. of the gantry of the therapeutic apparatus may further be controlled by the same. The radiotherapeutic apparatus is not limited to the linac.

While the best mode for carrying out the present invention has been described above, it will be understood by those who have general knowledge in the field of art to which the present invention belongs that changes and variations can be made in the invention without departing from the scope of the appended claims.

I claim:
1. In a radiotherapeutic system comprising
a source of radiation for radiating a selected region of a body;
a table comprising a first part on which said body is positioned for radiation treatment; and a second part;
an X-ray CT for providing a multislice scan to said body placed on said second part of said table for examination, to thereby provide multiple tomographic images of said body including regions thereof of interest; and
calculating means for using the multiple tomographic images of the body, including the regions of interest, to calculate three-dimensional coordinates of the center of the region of interest and the calculated perspective image thereof as seen from an imaginary center of projection corresponding to the position of the source of radiation; the improvement comprising
positioning means including projecting means for projecting three dimensional markings using at least three light beams to mark the surface of said body, one of said light beams projecting in one plane, and the other two light beams projecting on opposite sides of said body, with at least another of said light beams projecting in another plane which is perpendicular to said one plane, said marking being at places on the surface of said body determined by said three dimensional coordinates of the center of the region of interest;
means for drawing marks on the surface of said body at the places where the at least three light beams marked the surface of said body;
means for placing said body on said first part of said table in a position such that the center position of the region of interest as determined by the drawn marks coincides with the center of rotation of a gantry of said table;
collimator means having a variable aperature for emitting radiation therethrough to said body; and
controller means for controlling the aperature of said collimator means in accordance with the calculated perspective image data supplied by said calculating means so that the radiation is controlled so as to imping accurately on a selected region of said body; whereby diagnosis, planning and treatment are all performed on an on-line basis so that reliability, accuracy and execution are enhanced and error is decreased.

2. The system of claim 1, further comprising
means for supplying video signals of a radiated perspective image obtained by applying radiation through said body through said collimator means; and
means for displaying the radiated perspective image using the video signals and for displaying the calculated perspective image obtained by using the data from said calculating means, so that the radiated perspective image can be readily compared with the calculated perspective image.

* * * * *